United States Patent [19]

Martin

[11] Patent Number: 5,196,023

[45] Date of Patent: Mar. 23, 1993

[54] SURGICAL NEEDLE HOLDER AND CUTTER FOR AN ENDO-SUTURE, ENDO-LIGATURE OR THE LIKE

[76] Inventor: Werner Martin, Panoramastr. 6, 7207 Rietheim, Fed. Rep. of Germany

[21] Appl. No.: 650,889

[22] Filed: Feb. 5, 1991

[30] Foreign Application Priority Data

Feb. 5, 1990 [DE] Fed. Rep. of Germany ... 9001262[U]

[51] Int. Cl.⁵ .............................................. A61B 17/00
[52] U.S. Cl. .................................................. 606/148; 606/167; 606/174; 606/207
[58] Field of Search ............... 606/148, 139, 207, 206, 606/205, 138, 144, 147, 170, 174; 128/751; 225/91

[56] References Cited

U.S. PATENT DOCUMENTS

| | | | |
|---|---|---|---|
| 2,518,994 | 8/1950 | Miller | 606/205 |
| 2,998,649 | 9/1961 | Miller et al. | 606/138 |
| 4,669,470 | 6/1987 | Brandfield | 606/207 |
| 4,949,717 | 8/1990 | Shaw | 606/147 |

Primary Examiner—Stephen C. Pellegrino
Assistant Examiner—Jeffrey A. Schmidt
Attorney, Agent, or Firm—Bachman & LaPointe

[57] ABSTRACT

A surgical instrument capable of being used to guide a thread inside a body and to cut the thread comprises a forceps jaw having first and second opposed surfaces each provided with a serrated portion and a cutting portion.

2 Claims, 1 Drawing Sheet

SURGICAL NEEDLE HOLDER AND CUTTER FOR AN ENDO-SUTURE, ENDO-LIGATURE OR THE LIKE

BACKGROUND OF THE INVENTION

The invention relates to a surgical needle holder for an endo-ligature, endo-suture or the like with a forceps handle for actuating a forceps jaw composed of two jaw halves for holding a needle.

Needle holders of this type, especially Semm needle holders, are known to the market and widely used. The surgeon uses them to insert an endo-ligature, endo-suture or the like, this normally accompanying or assisting with an endoscopy.

The operation is performed merely by appropriate perforation of the peritoneum or the like, without using a scalpel to make a large incision, and the instrument is guided by a trocar.

However, especially when an endo-suture is inserted, either two trocars are necessary—one for the needle and thread holder and one for an appropriate scissor-like instrument for cutting off the thread after insertion of the suture—or the surgeon must change the instrument correspondingly frequently in one trocar.

Both are associated in every case with more effort by the surgeon and are relatively unpleasant for the patient. On the one hand, at least two perforations are required and, on the other hand, frequent changing of the instrument and the corresponding movement or change in position of the trocar may cause damage to muscles or vessels.

SUMMARY OF THE INVENTION

The inventor's object was to provide a surgical instrument which the surgeon is able to use both to guide a thread inside a body and to cut off this thread.

This object is achieved by providing a cutting device in the forceps jaw.

In the present exemplary embodiment, this cutting device follows serrations on the two jaw halves, which essentially serve to hold a needle.

However, the reverse arrangement is also within the scope of the invention, in which case the serrations would follow the cutter.

Every type of scissor-like cutting device is to be embraced by the concept of the invention. However, it is preferable for a ridge which has a cutter to be formed on one jaw half. This cutter is formed from the ridge by a concave grinding, the cutter itself having a concave design.

A recess in the other jaw half cooperates with the cutter or the ridge. When the forceps jaw is closed, the ridge with the cutter can enter this recess, with scissors being formed by the cutter with one edge of this recess. Of course, another design of the cutting device inside the forceps jaw is conceivable here too. For example, two ridges can each form one cutter, with the two cutters cooperating. In the region where the ridge on one jaw half engages in the recess on the other jaw half, a depression is formed in the latter. The effect of this depression is that, in the opened state of the forceps jaw, an approximately elliptical opening is produced with the concave shape of the cutter and forms an inlet for the thread to be cut off towards the opening of the forceps jaw. The effect of the concave shape of the cutter is that the introduced thread is no longer able to slip away towards the opening of the forceps jaw but is held.

This instrument can be used, on the one hand, to hold firmly and guide a needle or a thread with the front part of the jaw provided with serrations, while the adjoining part, the cutting part, is used to cut off the thread after the insertion of the suture.

BRIEF DESCRIPTION OF THE DRAWINGS

Other advantages, features and details of the invention are evident from the following description of the preferred exemplary embodiment and with the aid of the drawing, where

FIG. 4 shows further details of the forceps jaw.

DETAILED DESCRIPTION OF THE DRAWINGS

Figure 1:
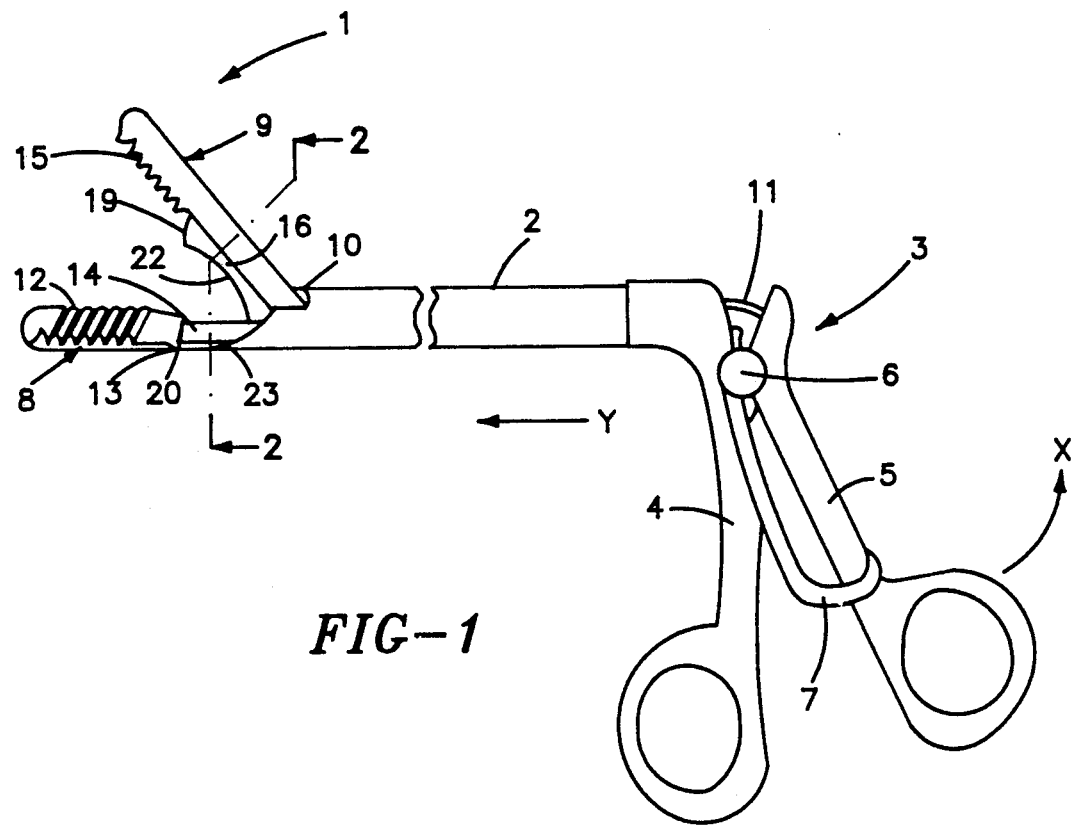
FIG. 1 shows a partially sectioned, perspective view of an instrument according to the invention with the forceps jaw open.

A surgical needle holder according to the invention, especially for producing an endo-suture and/or endo-ligature has, as shown in FIG. 1, a forceps jaw 1, a tube-like distance sleeve 2 and a scissors-like forceps handle 3.

Whereas one arm 4 of the forceps handle 3 is rigidly connected to the distance sleeve 2, one arm 5 is rotatable about an axis 6. A spring 7 is arranged so that, in the resting position, it holds the forceps jaw 1 in the closed position.

The forceps jaw 1 is formed from two jaw halves 8 and 9. One jaw half 8 is formed on the distance sleeve 2 and thus represents an extension of this distance sleeve 2.

Facing jaw half 8 is a movable jaw half 9 which is moved around an axis, which is not depicted in detail, within a recess 10 in the distance sleeve 2 with the aid of a steel core 11 or the like. When the arms 4 and 5 are spread in direction x by overcoming the force of the spring 7, the steel core 11 or the like is displaced in direction y within the distance sleeve 2. The core 11 is connected to jaw half 9 in such a way that the latter is opened by this forward displacement, i.e. reaches the spread position.

Jaw half 8 has serrations 12 which are connected towards the back, i.e. in the direction of the distance sleeve, to a depression 13. In the region of this depression 13 and as far as a region, which is not depicted in detail, of the axis part, which is likewise not depicted in detail, of the jaw half 9, jaw half 8 has an approximately rectangular recess or indented portion 14.

Figure 2:
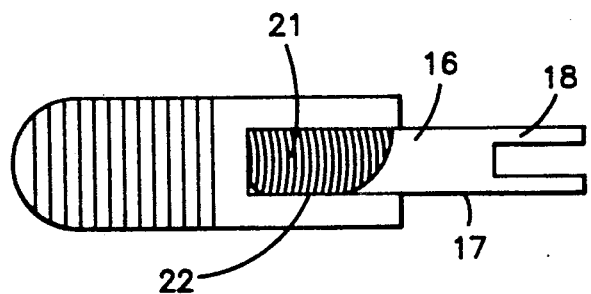
FIG. 2 shows a top view of a diagrammatically represented inner surface of a movable jaw half of the forceps jaw shown in FIG. 1.

Jaw half 8 is opposed by jaw half 9. It also has serrations 15, with the teeth being arranged so that, in the closed position, they engage in the teeth of the serrated region 12 of jaw half 8. Connected to the serrations 15 there is formed on jaw half 9 an approximately cuboidal projecting ridge 16 which projects above serrations 15 and which, as shown in FIG. 2, has in its extension 17 a receiving fork 18 for the steel core 11 which moves jaw part 9. This ridge 16 fits exactly in recess 14 in the closed position, with ridge 16 and recess 14 having a slightly convex shape in their front faces 19 and 20 respectively.

A concave grinding 21 is formed in ridge 16 in the region of ridge 16 which, in the closed position, enters the recess 14 in the region of the depression 13 and forms a sharp cutter or blade 22.

Figure 3:
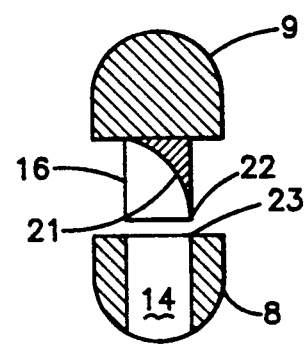
FIG. 3 shows a front view of the forceps jaw shown in FIG. 1.

When the forceps jaw 1 is closed, the cutter 22 runs exactly along a sharp edge 23 of the recess 14 (see FIG. 3 in particular) and, in this way, acts as scissors, with ridge 16 having the cutter 22 representing the upper blade.

Since, moreover, the cutter 22 which forms the upper blade has a slightly concave shape, when the forceps jaw 1 is open there is formed between ridge 16 or cutter 22 and the depression 13 an approximately elliptical opening into which a thread can be introduced from the direction of the opening of the forceps jaw 1 and can be cut off by closing the forceps jaw 1. This elliptical shaping of the cutter part means that an introduced thread is no longer able to slip out and is unavoidably cut off when the forceps jaw is closed.

With this instrument it is unnecessary, for holding the needle and thread and for cutting off the thread after insertion of the suture, either to change the instrument or to perform two interventions on the human body or use two trocars.

I claim:

1. A surgical instrument having a forceps handle, a forceps jaw comprising a stationary jaw and a pivotable jaw, and a steel core connecting said forceps handle with said pivotable jaw for pivoting said pivotable jaw for selectively opening and closing said forceps jaw upon actuation of said forceps handle, the improvement which comprises: said stationary jaw having a first surface provided with a serrated portion and an indented portion; and said pivotable jaw having a second surface opposed to said first surface of said stationary jaw provided with a serrated portion that cooperates with the serrated portion of the stationary jaw, and a projecting ridge portion, opposite said indented portion and received therein when said forceps pivotable jaw is closed said projecting ridge portion being provided with a recess surface extending from one side of said projecting ridge portion proximate to said second surface toward a second side of said projecting ridge portion remote from said second surface so as to define a cutter on said remote portion wherein said recess surface defines an opening for introducing a surgical thread into said indented portion of said stationary jaw when said projecting ridge portion is received in said indented portion.

2. A surgical instrument according to claim 1 wherein said recess surface is concave in shape.

* * * * *